US005348656A

United States Patent [19]

Podszun et al.

[11] Patent Number: 5,348,656
[45] Date of Patent: Sep. 20, 1994

[54] OPTICALLY ACTIVE BEAD POLYMERS CONTAINING FILLERS

[75] Inventors: Wolfgang Podszun, Cologne; Bruno Börner, Bergisch Gladbach; Rolf Grosser, Leverkusen; Walter Lange, Cologne; Michael Grosse-Bley, Cologne, all of Fed. Rep. of Germany

[73] Assignee: Bayer Aktiengesellschaft, Leverkusen, Fed. Rep. of Germany

[21] Appl. No.: 156,517

[22] Filed: Nov. 23, 1992

Related U.S. Application Data

[63] Continuation of Ser. No. 979,746, Nov. 23, 1992, abandoned.

[30] Foreign Application Priority Data

Dec. 3, 1991 [DE] Fed. Rep. of Germany ....... 4139747

[51] Int. Cl.$^5$ .................. B01D 15/08; C07B 57/00
[52] U.S. Cl. .................. 210/635; 210/656; 210/502.1; 210/198.2; 428/402; 524/847; 524/850; 523/203; 523/212; 523/214
[58] Field of Search ........ 210/635, 656, 198.2, 210/502.1; 428/402; 524/847, 850; 523/203, 212, 214

[56] References Cited

U.S. PATENT DOCUMENTS

| 4,140,653 | 2/1979 | Imura et al. ............... 252/430 |
| 4,724,207 | 2/1988 | Hou et al. ................ 435/177 |
| 4,873,301 | 10/1989 | Saotome et al. ........... 526/257 |
| 4,882,048 | 11/1989 | Blasecke et al. .......... 210/198.2 |
| 4,931,525 | 6/1990 | Schwartz et al. ........... 526/305 |
| 4,937,000 | 6/1990 | Börner et al. ............. 210/656 |
| 5,053,135 | 10/1991 | Boschetti et al. .......... 210/635 |
| 5,162,155 | 11/1992 | Berndt et al. ............. 428/405 |

FOREIGN PATENT DOCUMENTS

| 0084769 | 8/1983 | European Pat. Off. . |
| 0249078 | 12/1987 | European Pat. Off. . |
| 0379917 | 8/1990 | European Pat. Off. . |

OTHER PUBLICATIONS

R. Arshady (1991) J. Chromatogr. 586, 181–197 "Beaded Polymer Supports and Gels I. Manufacturing Techniques".
Blaschke, Chromatogr. Sci. 1988, 40, 179–198.
Chemical Abstracts, vol. 83, No. 4, Jul. 38, 1975, Columbus, Ohio, US. abstract No. 28896j, Balschke et al. "Chromatographic resolutions of racemates IV. . . . " p. 23, Col. 2 & Chem. Ber. vol. 108, No. 4, 1975, pp. 1188–1197.
"Preparative Methods of Polymer Chemistry", Wayne R. Sorenson and Tod W. Campbell, 1961.

*Primary Examiner*—Mark Nagumo
*Attorney, Agent, or Firm*—Sprung Horn Kramer & Woods

[57] ABSTRACT

The invention relates to optically active, pressurestable bead polymers containing fillers, and their use as adsorbents for the chromatographic resolution of enantiomeric mixtures (or racemates) into their enantiomers.

10 Claims, No Drawings

OPTICALLY ACTIVE BEAD POLYMERS CONTAINING FILLERS

This application is a continuation, Ser. No. 979,746, filed Nov. 23, 1992 now abandoned.

The invention relates to optically active, pressure-stable bead polymers containing fillers, and their use as adsorbents for the chromatographic resolution of enantiomeric mixtures (or racemates) into their enantiomers.

In recent years the resolution of biologically active substance racemates has gained increasing importance, since it has been shown that the enantiomers of a chiral active substance often differ in their actions and side effects.

In addition to the classical processes for racemate resolution, recently chromatographic racemate resolution has proven particularly suitable. Apart from the natural substance derivatives, for example based on cellulose, an increased number of synthetic, optically active, polymeric (meth)acrylamides have been employed as adsorbents (cf. Blaschke, Chromatogr. Sci. 1988, 40, 179 to 198).

Polymers based on optically active (meth)acrylic acid derivatives which are highly suitable as adsorbents for the resolution of racemates are described, for example, in EP-A-0,379,917.

Crosslinked, swellable bead polymers are particularly effective as a stationary phase for the preparative column-chromatographic resolution of racemates.

The adsorbents in bead form known until now only have, however, a limited mechanical stability. In particular their stability to pressure stress in the swollen state is unsatisfactory. This lack of pressure resistance leads in the case of practical application to the fact that at high flow rates (to achieve a high space-time yield), as a result of deformation of the bead polymers the columns can finally block. The limitation of the maximum flow rate during chromatography on conventional swollen bead polymers restricts the industrial application of this method and is accompanied by economic disadvantages.

The object of the present invention is the provision of optically active bead polymers having good separating properties and having improved mechanical properties, in particular having an improved pressure resistance.

This object is achieved by optically active crosslinked bead polymers, which are characterised in that they contain an amount of 2 to 60% by weight, preferably 5 to 30% by weight, of inorganic filler.

It was to a large extent surprising that in addition to decisively improved mechanical properties, in particular pressure stability, the bead polymers according to the invention have a good swelling power and excellent separating properties in spite of the incorporation of fillers.

The average particle diameter of the optically active bead polymers according to the invention is 1 to 800 μm, preferably 5 to 400 μm, particularly preferably 10 to 200 μm.

Suitable inorganic fillers are insoluble, finely divided, crystalline or amorphous, inorganic compounds having an average particle size of 3 nm to 10 μm, preferably 10 nm to 5 μm.

Examples of suitable fillers according to the invention are hydroxides, oxides, carbonates, sulphates and phosphates of metals, such as aluminium hydroxide, aluminium oxide, aluminium oxide hydrate, titanium dioxide, zirconium dioxide, calcium carbonate, dolomite, calcium sulphate, barium sulphate, calcium phosphate and zirconium phosphate. Silicate fillers such as, for example, kaolin, calcined kaolin, mica, wollastonite, calcium silicate, aluminium silicate, sodium alumino-silicate, zirconium silicate, quartz flour and amorphous silica, and in addition finely ground glasses and glass ceramics are preferred. Microfine silica obtained by flame hydrolysis, which is obtainable as a commercial product, for example, under the name Aerosil or HDK (highly disperse silicic acid) is particularly preferred.

The size of the specific surface area of the inorganic filler is important for the quality and the separating properties of the bead polymers according to the invention. The specific surface area should be 30 to 500 $m^2/g$. preferably 50 to 400 $m^2/g$, measured by the BET method (gas adsorption).

The inorganic fillers are preferably used in adhesion promoter-treated form. Suitable adhesion promoters are, for example, silane and titanium compounds, such as trimethylchlorosilane, hexamethylenedisiloxane, 3-aminopropyltrimethoxysilane, butyl titanate and isopropyl titanate. Particularly preferred adhesion promoters are those having polymerisable groups, such as vinyltrimethoxysilane, vinyltriethoxysilane, vinylethyldiethoxysilane, allyltriethoxysilane, γ-methacryloxypropyltrimethoxysilane, γ-methacryloxypropyltriethoxysilane, γ-acryloxypropyltrimethoxysilane, γ-acryloxypropyltriethoxysilane and γ-methacryloxypropylmethyldiethoxysilane.

In the preparation of the bead polymers according to the invention, polymerisable derivatives of optically active amines or amino alcohols having up to 20° C. atoms or of amino acid esters and amino acid amides which are derived from amino acids having up to 15 C atoms and whose ester or amide radicals have up to 20° C. atoms are preferably employed.

Preferred polymerisable monomers of the general formula (II)

which may be mentioned are those in which
$R^1$ and $R^2$ are identical or different and each represent hydrogen, $C_1-C_{10}$-alkyl, $C_3-C_{12}$-cycloalkyl, $C_5-C_{14}$-aryl, $C_4-C_5$-heteroaryl having 1 to 2 identical or different heteroatoms from the group comprising nitrogen, oxygen and sulphur or represent aralkyl having up to 12 C atoms, where the radicals are optionally mono-to trisubstituted by alkyl, alkoxy in each case having 1 to 4 C atoms, hydroxyl, halogen, trifluoromethyl or trifluoromethoxy and
$R^3$ represents a polymerisable radical.

Of particular interest are compounds of the general formula (II), in which $R^3$ represents an olefinically unsaturated radical such as, for example, a radical from the group comprising acryloyl, methacryloyl, fluoroacryloyl, vinylbenzoyl or propenylbenzoyl.

Likewise particularly suitable compounds of the general formula (II) are those from the group comprising the optically active, naturally occurring amino acids and their esters and amides.

Very particularly preferred optically active compounds of the formula (II) are methyl(meth)-acrylamide, 1-cyclohexylethyl-(meth)acrylamide, 1-phenylethyl-(meth)acrylamide, N-(meth)acryloyl-phenylalanine ethyl ester, N-(meth)acryloyl-phenylalanine diethylamide, 2-(methyl)ethenyl-4-methyl-5-phenyl-2-oxazoline, N-(meth)acryloyl-valine t-butyl ester, N-(meth)acryloyl-leucine t-butyl ester, N-(meth)acryloyl-phenylalanine t-butyl ester, N-(meth)acryloyl-alanine menthyl ester, N-(meth)acryloylphenylalanine menthyl ester, N-fluoroacryloyl-alanine bornyl ester, N-fluoroacryloyl-alanine fenchyl ester, N-(meth)acryloyl-alanine menthylamide, N-(meth)acryloyl-methionine 1-phenylethylamide, N-(meth)acryloyl-leucine menthylamide, N-(meth)acryloyl-isoleucine menthylamide, N-methacryloyl-leucine anilide, benzyl N-(meth)acryloyl-amino-penicillanate sulphoxide and N-(meth)acryloyl-phenylglycine propylamide.

The polymerisable compounds disclosed in the Patent Specifications EP-249,078, EP-281,234, EP-0,379,917, German Offenlegungsschrift 2,500,323 and German Offenlegungsschrift 3,930,344 are also very highly suitable.

The optically active, pressure-stable bead polymers according to the invention contain 30 to 95% by weight, preferably 50 to 90% by weight (relative to the weight of the bead polymers) polymer content of identical or different polymerisable compounds of the formula (II), 2 to 60% by weight, preferably 4 to 30% by weight of inorganic filler and 3 to 25% by weight, preferably 6 to 20% by weight, of a crosslinking agent.

The optically active, crosslinked bead polymers according to the invention are prepared by customary methods, for example by a) suspending the inorganic filler, if appropriate treated with adhesion promoters, in a mixture of optically active, polymerisable compounds of the formula (II), a crosslinking agent and a diluent using high shear forces, b) activating the mixture obtained with a free-radical promoter and dispersing in an aqueous medium using a protective colloid and then c) polymerising the dispersion obtained by heating to the decomposition temperature of the free-radical promoter.

Suitable crosslinking agents are preferably compounds which contain at least two polymerisable groups, preferably two vinyl groups. Preferred crosslinking agents are alkanediol diacrylates such as 1,6-hexanediol diacrylate, 1,4-butanediol diacrylate, 1,3-propanediol diacrylate or 1,2-ethylene glycol diacrylate or alkanediol dimethacrylates such as 1,4-, 1,3- or 2,3-butanediol dimethacrylate, 1,3-propanediol dimethacrylate or 1,2-ethylene glycol dimethacrylate, aromatic divinyl compounds such as, for example, divinylbenzene, divinylchlorobenzene, divinyltoluene, dicarboxylic acid esters such as divinyl adipate, divinyl benzenedicarboxylate, divinyl terephthalate, N,N'-alkylenediacrylamides such as N,N'-methylenediacrylamide, N,N'-ethylenediacrylamide, N,N'-methylenedimethacrylamide, N,N'-ethylenedimethacrylamide, N,N'-dimethyl-ethylenediacrylamide or piperazinediacrylamide. Other suitable crosslinking agents are multifunctional crosslinkers such as trimethylolpropane triacrylate, trimethylolpropane trimethacrylate, pentaerythritol triacrylate, pentaerythritol tetraacrylate, pentaerythritol trimethacrylate, pentaerythritol tetramethacrylate or N,N',N''-tris-acryloyl-perhydrotriazine.

The crosslinking agent is employed in amounts from 0.5 to 50 mol %, preferably 1 to 30 mol %, particularly preferably 3 to 20 mol % (relative to the sum of the optically active compounds of the formula (II) and the crosslinking agent). This corresponds to an amount of 3 to 25% by weight, relative to the weight of the bead polymer.

By means of the type and amount of crosslinking agent, the degree of swelling (Q) of the bead polymers can be adjusted according to customary methods.

In practical use, bead polymers having a degree of swelling from 1.1 to 12.0, preferably from 1.5 to 8.0, in particular from 2.0 to 6.0, have proven suitable.

The degree of swelling Q is defined as follows:

$$Q = \frac{\text{Volume of swollen bead polymer}}{\text{Volume of unswollen bead polymer}}$$

Suitable swelling agents are water-immiscible, inert organic liquids. Those which may be preferably mentioned are aliphatic or aromatic hydrocarbons having up to 20 C atoms, such as hexane, heptane, isodecane, benzene or toluene, halogenohydrocarbons such as di-, tri- and tetrachloromethane or 1,2-dichloroethane, esters such as methyl acetate, butyl acetate or dialkyl carbonates and water-insoluble ketones such as methyl isobutyl ketone or cyclohexanone. The weight ratio of diluent to the optically active, polymerisable compounds (II) is 0.5:1 to 30:1, preferably 1.5:1 to 10:1.

Suitable free-radical promoters in step b) are the customary free-radical promoters. Those preferred are peroxides such as, for example, dibenzoyl peroxide, dilauryl peroxide or di-orthotolyl peroxide, peresters such as tert-butyl perpivalate or tert-butyl peroctanoate, or azo compounds such as, for example, azobisisobutyronitrile (AIBN). Mixtures of various free-radical promoters can also be used.

Suitable protective colloids are natural and synthetic, water-soluble, high molecular weight substances. Those preferred are synthetic polymers, such as polyvinyl alcohol and partially hydrolysed polyvinyl acetates, and in addition polyvinylpyrrolidone and copolymers of (meth)acrylic acid and alkyl (meth)acrylates whose acid groups are completely or partially neutralised with ammonia or alkali metal hydroxide.

During the polymerisation in step c), a ratio of water phase to the organic phase of 20:1 to 1:1, preferably 10:1 to 2:1, is maintained. Polymerisation is preferably carried out under an inert gas atmosphere, for example under nitrogen or argon. The polymerisation temperature is 30° to 100° C., preferably 40° to 80° C. In many cases it is advantageous to work at the boiling point of the diluent. The polymerisation period is between 1 and 24 hours, preferably between 3 and 12 hours. The bead polymer according to the invention can be separated off in a customary manner after polymerisation has taken place, for example by filtration or sedimentation of the liquid phase. For purification, the bead polymer is thoroughly washed with water and with inert organic solvents such as methanol, ethanol, toluene, dichloromethane, trichloromethane or acetone and then dried.

The use of the optically active bead polymers according to the invention for the chromatographic resolution of racemic mixtures into their enantiomers is likewise a subject of the present invention.

The capacity of the polymers for resolution of racemates is expressed by the capacity ratio ($k'_{1(2)}$ values) for the two enantiomers (1) and (2) and the enantioselectivity value α resulting therefrom. These chromatographic parameters are defined as follows:

$$\text{Capacity ratio } K_{1(2)}' = \frac{t_{1(2)} - t_0}{t_0}$$

$$\text{Enantioselectivity } \alpha = \frac{k_2'}{k_1'}$$

$t_0$ = dead time of the column, $t_{1(2)}$ = retention time of the first-eluted enantiomer 1 or of the later-eluted enantiomer 2.

The preparative resolution of racemic mixtures into their optical antipodes using the polymers according to the invention is preferably performed by column chromatography. It is particularly advantageous for this purpose to perform the chromatographic resolution using bead polymers of a certain particle size distribution; good separating efficiencies are obtained with bead polymers of a particle size distribution from 5 to 200 μm, preferably 15 to 100 μm.

The working methodology of column-chromatographic resolution is known. Customarily, the polymer is suspended in eluent and the suspension is packed in a glass column. After running off the eluent, the racemate to be resolved, dissolved in the eluent, is applied to the column. This is then eluted with eluent and the enantiomers in the eluate are detected photometrically and/or polarimetrically by means of suitable flow cells.

Eluents used are customarily organic solvents or solvent mixtures which swell the polymer employed as the absorbent and dissolve the racemate to be resolved. Examples which may be mentioned are: hydrocarbons such as benzene, toluene or xylene, ethers such as diethyl ether, tertbutyl methyl ether, dioxane or tetrahydrofuran, halogenohydrocarbons such as di- or trichloromethane, acetone, acetonitrile or ethyl acetate, alcohols such as methanol, ethanol, n-propanol, isopropanol or n-butanol, or else mixtures of the solvents mentioned. Mixtures of toluene with tetrahydrofuran, dioxane or isopropanol have proven particularly suitable.

EXAMPLES

EXAMPLE 1

Preparation of a filler-containing bead polymer from N-acryloyl-L-phenylalanine d-menthyl ester 13.8 g of N-Acryloyl-L-phenylalanine d-menthyl ester and 1.2 g of ethylene glycol dimethacrylate are dissolved in 37.5 g of trichloromethane. Using a high-speed stirrer, 1.7 g of microfine silica (BET surface area 130 m$^2$/g, treated with 5% γ-methacryloxypropyltrimethoxysilane) are incorporated into this solution. After addition of 0.3 g of azobisisobutyronitrile, the mixture obtained is dispersed in a solution of 5 g of polyvinyl alcohol (degree of hydrolysis: 88%) in 100 ml of water with stirring at 450 rpm. The apparatus is evacuated several times and filled with nitrogen. The mixture is then polymerised for 10 hours at 55° C. under nitrogen. The reaction mixture is then diluted with 2 l of water and the liquid phase is decanted off after the bead polymer has settled. The bead polymer is freed from the fine grain material (particles having a particle size <5 μm) by suspending 4 times in water and decanting off and is dried at 60° C. after intensive washing with acetone.

Yield: 12.6 g
Average particle size: 25 μm
Bulk density: 2.1 ml/g
Degree of swelling: 2.57

EXAMPLE 2

Preparation of a filler-containing bead polymer from N-methacryloyl-L-leucine t-butyl ester Example 1 was repeated, a solution of 13.7 g of N-methacryloyl-L-leucine t-butyl ester and 1.3 g of ethylene glycol dimethacrylate in 37.5 g of trichloromethane being employed.

Yield: 14.6 g
Average particle size: 40 μm
Bulk density: 2.1 ml/g
Degree of swelling: 2.43

EXAMPLE 3

Preparation of a filler-containing bead polymer from N-methacryloyl-L-methionine-1-menthylamide Example 1 was repeated, a solution of 13.7 g of N-methacryloyl-L-methionine-1-menthylamide and 1.3 g of ethylene glycol dimethacrylate in 37.5 g of trichloromethane being employed.

Yield: 15.1 g
Average particle size: 36 μm
Bulk density: 1.85 ml/g
Degree of swelling: 2.00

Comparison Example A (without filler)

Preparation of a bead polymer from N-acryloyl-L-phenylalanine d-menthyl ester without filler Example 1 was repeated, but no silica was employed.

Yield: 11.1 g
Average particle size: 28 μm
Bulk density: 1.8 ml/g
Degree of swelling: 2.33

EXAMPLE 4

Example 1 was repeated, 0.8 g of the same microfine silica and a solution of 13.0 g of N-acryloyl-L-phenylalanine d-menthyl ester and 2.0 g of ethylene glycol dimethacrylate in 37.5 g of trichloromethane being employed.

Yield: 11.1 g
Average particle size: 30 μm
Bulk density: 1.6 ml/g
Degree of swelling: 2.31

Example 5

Example 1 was repeated, 3.75 g of the same microfine silica and a solution of 13.6 g of N-acryloyl-L-phenylalanine d-menthyl ester and 1.4 g of ethylene glycol dimethacrylate in 37.5 g of trichloromethane being employed.

Yield: 12.6 g
Average particle size: 60 μm
Bulk density: 1.7 ml/g
Degree of swelling: 2.12

Use Example:

The following test racemates were used for the chromatographic resolutions:

Racemate No. 1: 3-(4-chlorophenylsulphonamide)-9-(2-carboxyethyl(-1,2,3,4-tetrahydrocarbazole Racemate No. 2: 3,5-dinitrobenzoylleucine The bead polymers were employed in a glass column (internal diameter 1.2 cm; bed height of the packing 30–32 cm). It was eluted with toluene/tetrahydrofuran mixtures (eluent a toluene/THF 1:1; eluent b toluene/THF 2:1; eluent c toluene/THF 3:1); the flow rates were in each case 0.5 ml/min. The results obtained in the chromatographic resolution of the test racemates with the aid of the filler-containing, optically active bead polymers according to the invention and with the polymer from Comparison Example A and the eluents used are collated in Table 1.

The pressure resistance tests were carried out following the resolution tests— after removal of the detector. Starting at 0.5 ml/min, the flow was increased by 0.5 ml/min after 30 min in each case until the pressure decrease over the column was 8 bar. The maximum flow determined at this final pressure is likewise given in the Table.

TABLE 1

| Adsorbent according to Ex. | Test racemate | (resolution results) Enantio-selectivity α | Capacity ratio | Eluent | Maximum flow (ml/min) |
|---|---|---|---|---|---|
| 1 | 1 | 1.83 | 0.59 | b | 8.5 |
| 2 | 1 | 1.69 | 1.91 | a | >10 |
| 3 | 2 | 1.83 | 0.70 | c | >10 |
| 4 | 1 | 1.91 | 0.57 | b | 10 |
| 5 | 1 | 1.85 | 0.55 | b | >10 |
| A | 1 | 1.75 | 0.49 | b | 2.0 |

We claim:

1. Optically active crosslinked bead polymers made of water-dispersible monomers, characterised in that they contain an amount of 2 to 60% by weight of inorganic filler.

2. Optically active crosslinked bead polymers according to claim 1, which contain an amount of 5 to 30% by weight of inorganic filler.

3. Bead polymers according to claim 1, characterised in that as inorganic filler they contain insoluble crystalline or amorphous, inorganic compounds having an average particle size of 3 nm to 10 μm.

4. Bead polymers according to claim 1, having an average particle diameter of 1 to 800 μm.

5. Bead polymers according to claim 1, characterised in that the inorganic filler comprises hydroxides, oxides, carbonates, sulphates, phosphates or silicates of metals, silicas or finely ground glasses or glass ceramics.

6. Bead polymers according to claim 1, characterised in that they contain inorganic fillers which have been treated with adhesion promoters from the silane and/or titanium compounds group.

7. Bead polymers according to claims 1 characterised in that they contain polymerisable derivatives of optically active amines, amino alcohols, amino acid esters or amino acid amides.

8. Bead polymers according to claim 1, characterised in that they contain 30 to 95% by weight (relative to the weight of the bead polymers) polymer content of identical or different polymerisable compounds.

9. Method for the preparation of optically active crosslinked bead polymers according to claim 1, characterised in that the inorganic filler, if appropriate treated with adhesion promoters, is suspended in a mixture of optically active polymerisable compounds, a crosslinking agent and a diluent, the mixture obtained is activated with a free-radical promoter and dispersed in an aqueous medium using a protective colloid and the dispersion obtained is then polymerised by heating to the decomposition temperature of the free-radical promoter.

10. In the chromatographic resolution of an enantiomer mixture into its enantiomers by passage through a column containing polymer beads, the improvement wherein said beads are bead polymers according to claim 1.

* * * * *